United States Patent [19]

Tannenbaum

[11] Patent Number: 4,977,895
[45] Date of Patent: Dec. 18, 1990

[54] ELECTRICAL APPARATUS FOR MEDICAL TREATMENT

[75] Inventor: Joseph Tannenbaum, Jerusalem, Israel

[73] Assignee: Ely Shavit Pasternak, Holon, Israel; a part interest

[21] Appl. No.: 354,766

[22] Filed: May 22, 1989

[51] Int. Cl.$^5$ .............................................. A61N 1/00
[52] U.S. Cl. ................................ 128/421; 128/419 R
[58] Field of Search ................... 128/421, 422, 419 R, 128/420.5

[56] References Cited

U.S. PATENT DOCUMENTS

| | | | |
|---|---|---|---|
| 4,711,243 | 12/1987 | Schafer | 128/420.5 |
| 4,769,881 | 9/1988 | Pedigo et al. | 128/419 R |
| 4,841,972 | 6/1989 | Masaki | 128/421 |
| 4,844,075 | 7/1989 | Liss et al. | 128/419 R |

*Primary Examiner*—Francis Jaworski
*Assistant Examiner*—Goerge Manuel
*Attorney, Agent, or Firm*—Edward Langer

[57] ABSTRACT

An electrical neuro-stimulator which operates using pulse generators for providing a master frequency, a carrier frequency, a first modulation frequency and a second modulation frequency. The pulse width and pulse rate are adjustable, and a pair of multivibrators produces a pulse train output with an adjustable number of impulses by adjustment of the carrier frequency, which also increases the average applied power and the penetration factor. The master and carrier oscillators of the pulse generator operate asynchronously, and a digital mixer is provided for combination of these frequencies with a slightly random appearance, thus avoiding accommodation or adaptation while maintaining a constant energy at any frequency. The first modulation frequency provides a triangular form of amplitude modulation of the pulse train waveform envelope. A 180 degree shift in this waveform is provided by a time lag introduced on the second channel, such that accommodation of the nerves is avoided. By combination of high and low-pass filters, the envelope of the pulse train waveform is given an increasing amplitude from its initial value during a predetermined interval. This avoids shock sensation on the skin when the pulses are first applied, since the initial tissue impedance is higher and the voltage applied must necessarily be higher to maintain constant current. A set of specially-designed pulse transformers is provided to maintain the optimal pulse waveform shape when the tissue impedance changes, providing compensation via a reactive componment.

15 Claims, 3 Drawing Sheets

ELECTRICAL APPARATUS FOR MEDICAL TREATMENT

FIELD OF THE INVENTION

The present invention relates to electrical apparatus for neuromuscular stimulation by electrical pulses, and more particularly, to a novel electrical stimulator device for relieving pain and activating muscle fibers by delivery of modulated pulses of relatively high average power, with reduced skin irritation and a higher penetration factor, reaching the large myelinated nerves.

BACKGROUND OF THE INVENTION

The prior art contains many electrical stimulation devices based on the use of pulse generators for transcutaneous application of electrical pulses to the nerves and muscles. Examples of these are listed below:

U.S. Pat. No. 4,699,143 to Dieken et al;
U.S. Pat. No. 4,230,121 to Stanton;
U.S. Pat. No. 4,201,151 to Keller;
U.S. Pat. No. 4,173,741 to Kameny;
U.S. Pat. No. 4,144,893 to Hickey;
U.S. Pat. No. 4,121,594 to Arp et al;
U.S. Pat. No. 4,062,365 to Kameny;
U.S. Pat. No. 4,765,322 to Charmillot et al;
U.S. Pat. No. 4,763,656 to Nauman; and
U.S. Pat. No. 4,408,608 to Daly et al.

In addition to the above listed patents, my previous U.S. Pat. No. 4,233,986 disclosed apparatus and methods for controlling pain by transcutaneous electrical stimulation, based on use of a pulse generator with various modulation techniques including frequency and pulse width modulation.

In U.S. Pat. No. 3,983,881 to Wickham, the energy content of each pulse train is modulated by increase and decrease of the pulse width, for gradual contraction and relaxation of the muscles. U.S. Pat. No. 4,759,368 to Spanton et al discloses independence between variation of the pulse rate and modulation of the pulse amplitude and width, to avoid the phenomenon of accomodation in nerve stimulation.

U.S. Pat. No. 4,431,000 to Butler et al discloses application of an irregular pulse train by use of a pseudorandom pulse generator, with the average pulse rate on the order of the alpha rate, and is adapted to allow the nerves to repolarize while reducing the effect of variables such as skin resistance. The base pulse rate, pulse width and amplitude are also adjustable.

A study of the wide range of neuro-stimulators reveals that most of these instruments use a pulse transformation technique, with low voltage provided by a battery source. In order to reduce the size of the instrument by reducing the pulse transformer dimension, a miniature high frequency ferrite core is used, but this limits the application of pulse shaping and stabilization techniques. The early transcutaneous nerve stimulators (TNS) operated within the 40-300 microseconds pulse width range, with a frequency range of 1-150 pulse/-second. The problem with these instruments is that they do not account for basic neurophysiological behavior, and exhibit low efficacy, causing pain and irritation of the skin, since they operate on the skin surface area where the pain receptors are concentrated.

It is known from the behavior of the nervous system that electrical stimulation of the large myelinated nerves is more effective in reducing pain, since this provides access to a higher level of the nervous system via the synapses, closer to the spinal cord and the brain.

It is therefore an object of the present invention to provide a neuro-stimulator device which reduces pain, while achieving higher penetration of the biologicial tissue to reach the large nerves at a higher energy level without causing skin irritation.

It is a further object of the invention to achieve better coordination between the electrical pulses and the physioligical behavior of the nervous system, by accounting for the reaction of nervous system to the applied pulse waveforms.

Similarly, it is an object of the invention to achieve better coordination between the electrical pulses and the physiological behavior of the muscular system.

It is still a further object of the invention to avoid the phenomenon of accomodation so that the nerves and/or muscles remain responsive to the applied electrical stimulation.

It is yet another object of the invention to achieve electrical stimulation at a constant current via compensation for the changes in the tissue impedance.

SUMMARY OF THE INVENTION

Accordingly, it is a principal object of the present invention to overcome the above-mentioned disadvantages and provide a novel electrical neuro-stimulator capable of increasing the average applied power without irritation and pain, thereby achieving increased penetration of the tissue and stimulation of the large myelinated nerves. Novel electronic circuitry achieves a pulse waveform related to the physiological behavior of the nervous system, and a constant current is provided based on compensation for the changes in tissue impedance.

In accordance with a preferred embodiment of the present invention, there is provided electrical neurostimulation apparatus comprising:

first pulse generation means for providing a first variable frequency and pulse width output;

second pulse generation means for providing a second variable frequency and pulse width output;

switching means for providing a series of pulse trains as a combination of said first and second pulse width outputs on at least one output channel;

means for modulating said series of pulse trains so as to provide a pulse waveform envelope having an increasing amplitude during a predetermined interval; and current amplification means for providing said modulated series of pulse trains to at least one pair of electrodes with substantially constant current in relation to tissue impedance for increased penetration, said amplified modulated series of pulse trains providing electrical stimulation of the large myelinated nerves with significantly increased energy at relatively low skin irritation and pain levels.

In the preferred embodiment, the inventive electrical neuro-stimulator comprises pulse generators for providing a master frequency, a carrier frequency, a first modulation frequency and a second modulation frequency. The pulse width and pulse rate are adjustable, and a switching means comprising a pair of multivibrators produces a pulse train output. The number of impulses in the pulse train is adjusted by adjustment of the carrier frequency, which also increases the average applied power and the penetration factor. Since the master and carrier oscillators of the pulse generator operate asynchronously, a digital mixer is provided for combination of the master and carrier frequencies with a slightly random appearance, thus avoiding accomodation or adaptation. The digital mixer also maintains a constant energy at any frequency.

The first modulation frequency provides a triangular form of amplitude modulation of the pulse train waveform envelope. A 180 degree shift in this waveform is provided by a time lag introduced on the second channel, such that accomodation of the nerves is avoided. The inverse application of the two channel waveform to the extensor and flexor muscles has a beneficial effect on the circulatory system.

By combination of high and low-pass filters, the envelope of the pulse train waveform is given an increasing amplitude from its initial value during a predetermined interval. This avoids shock sensation on the skin when the pulses are first applied, since the initial tissue impedance is higher and the voltage applied must necessarily be higher to maintain constant current.

The current amplification means comprises FET transistor amplifiers which feed a set of specially-designed pulse transformers which maintain the optimal pulse waveform shape when the tissue impedance changes, providing compensation via a reactive component.

A second modulation frequency, typically 100 Khz, is provided in the pulse train to further reduce the dielectrical losses of the tissue, ensuring increased penetration.

A feature of the invention is the provision of an electronic helipot potentiometer for adjustment of the current regulation with an infinitely smooth ratio, without the use of mechanical adjustment as provided by conventional multi-turn potentiometers.

Another feature of the invention is the provision of a visual indication corresponding to the level of the applied voltage, in the form of a group of individual LEDs. Several or all of the LEDs are lit in accordance with the level of the voltage applied to the surface electrodes, providing a rough measurement of the pulse energy output.

Based on the novel design of the present invention, medical treatment using electrical stimulation is more effective, since the various pulse programs and combinations of pulse trains are provided in accordance with recognized physiological behavior of the nervous system. The wide flexibility of the device operation answers various needs of the medical and scientific communities where electrical stimulation is an accepted form of therapeutic treatment.

Other features and advantages of the invention will become apparent from the drawings and the description contained hereinbelow.

BRIEF DESCRIPTION OF THE DRAWINGS

For a better understanding of the invention, reference is made to the accompanying drawings, in which like numerals designate corresponding elements or sections throughout, and in which.

DETAILED DESCRIPTION OF THE PREFERRED EMBODIMENT

As described further herein, the inventive electrical neuro-stimulator is a therapeutic device for treatment of pain and activation of muscle fibers, with the capability of increasing blood flow in the circulatory system. This is achieved by relatively high average energy and pulse energy, with greater penetration, causing a more direct effect on the large myelinated nerves. The electronic circuitry is designed to achieve combined pulse waveforms which are related to the physiological behavior of the nervous system, with the provision of constant current based on compensation for the changes in tissue impedance.

Figure 1:
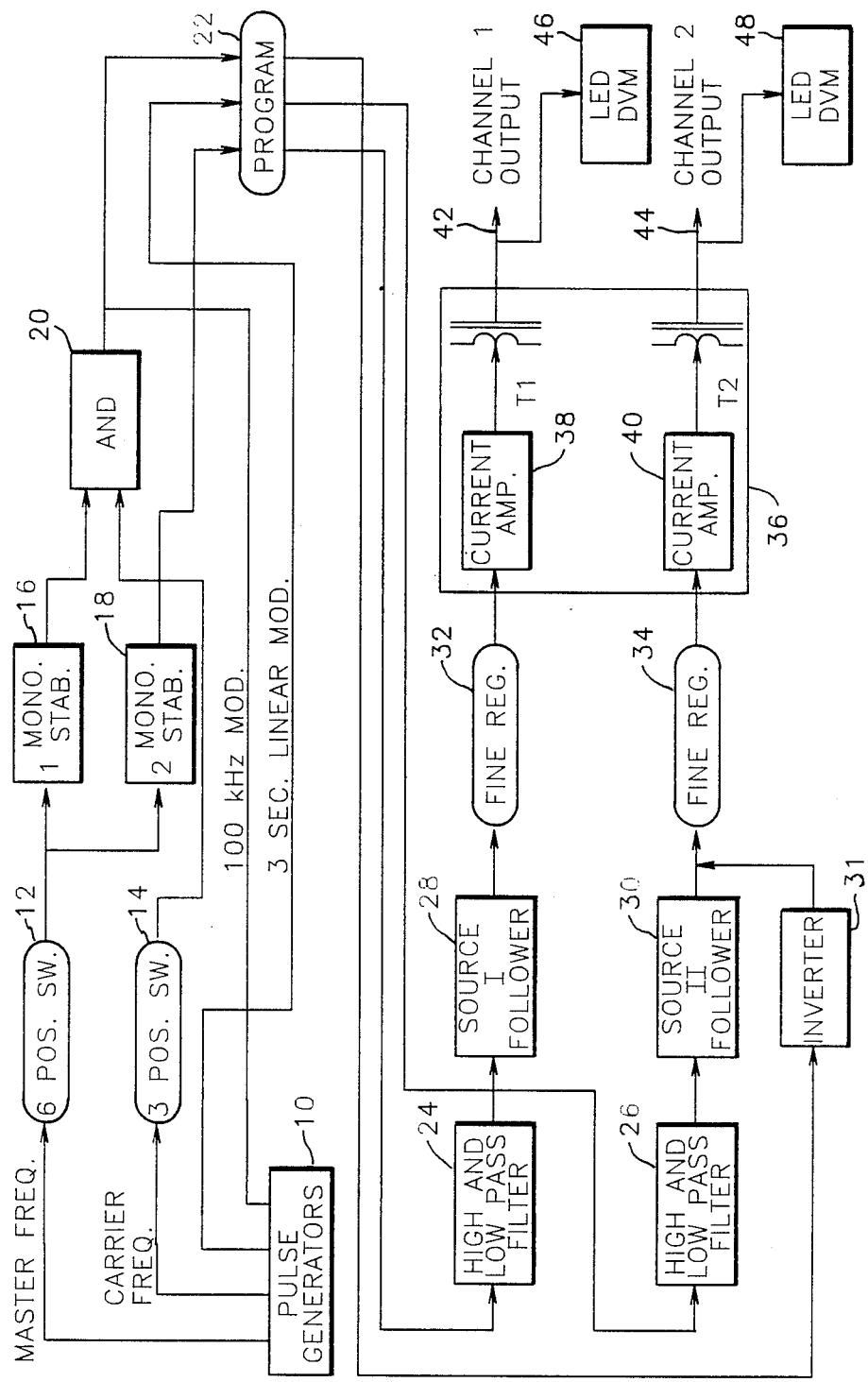
FIG. 1 shows an overall electronic block diagram of a preferred embodiment of a neuro-stimulator constructed and operated in accordance with the principles of the present invention.

Referring now to FIG. 1, there is shown a block diagram of a preferred embodiment of the present invention. The inventive neuro-stimulator device is designed provide pulse waveform output on two channels I and II, each of which is fed to an electrode for application of the pulse output to the skin. A pulse generator block 10 forms the heart of the device and provides a pulse output at a master frequency (A) and a carrier frequency (B), each of which can be determined by adjustment of a respective one of six and three-position switches 12 and 14. The master frequency is fed to a pair of monostable multivibrator blocks 16 and 18 which determine the pulse train duration of the master frequency. These blocks 16 and 18 also introduce a very fast rise and fall time for the individual pulses forming the pulse train, on the order of approximately 1 microsecond, which is important to overcome the dielectric effect of the biological tissue.

A third frequency (C) is also generated by pulse generator 10, which is modulated by a three second linear modulation, as described further herein. A fourth optional frequency (D) is also provided by pulse generator 10, for modulation of the output of each of channels I and II, in order to improve the penetration of the pulses through the dielectric constant of the biological tissue.

A digital mixer block 20 (AND gate) is fed by both master and carrier frequencies A and B, and because each of these frequencies is generated asynchronously, the output of digital mixer block 20 is provided with a slightly random appearance of the combined pulses. The digital mixer 20 is also designed to maintain the pulse waveform with constant energy output in any frequency, such that the period of pulse train duration is equivalent to the interval between successive pulse trains.

The program switch 22 block comprises a manual switching means for providing the generated pulse trains in various combinations to each of channels I and II via the pair of filter blocks 24 and 26. The source follower blocks 28 and 30 operate as filters which provide amplitude modulation and waveshaping to maintain the pulse train envelope with a desired amplitude variation. An inverter block 31 has its input connected to the program switch 22 and its output connected to a fine regulation block 32 of channel II. Inverter block 31 provides a predetermined time lag between the output of channels I and II, for achieving a desired physiological response.

Each of fine regulation blocks 32 and 34 comprises a current regulator for adjusting the internal impedance of a high impedance current source 36, which comprises a pair of power current amplifiers 38 and 40, corresponding to each of channels I and II. The output of each of current amplifiers 38 and 40 is fed to a respective one of a pair of specially-designed ferrite-type pulse transformers T1 and T2. Each of pulse transformers T1 and T2 comprises three individual coils, a primary, secondary and compensation coil.

The output of pulse transformers T1 and T2 is applied to electrodes 42 and 44 which are attached to the skin for therapeutic treatment using the neuro-stimulator device of the invention. To estimate the energy applied during the treatment, the actual potential applied to the electrodes must be measured, and for this purpose, a simple digital voltmeter arrangement is provided by blocks 46 and 48. These blocks each comprise a hex Schmitt trigger circuit, which activates a group of six LEDs for providing a visual indication of the applied potential.

Figure 2A:
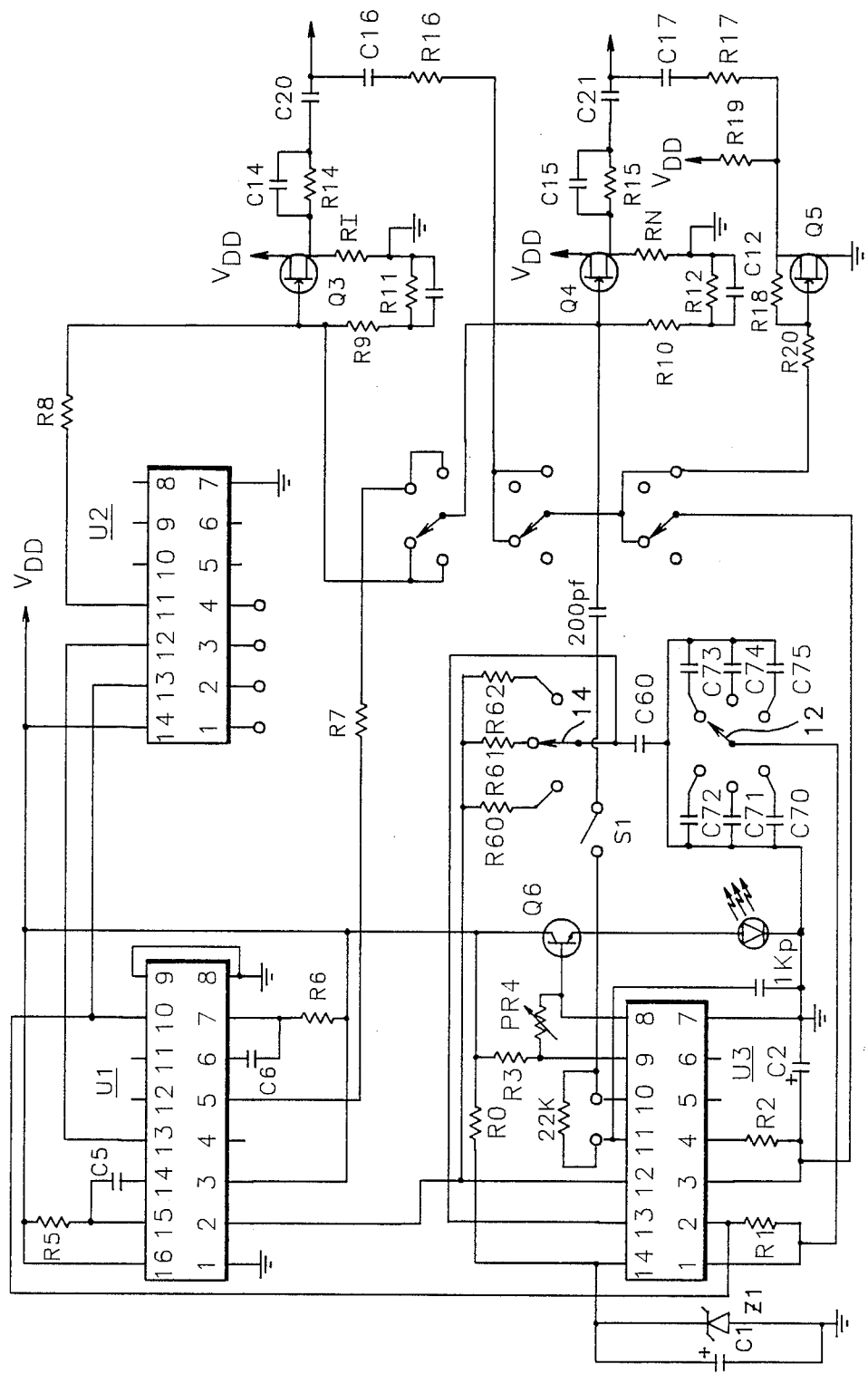
FIG. 2 is an electronic circuit schematic of the neuro-stimulator of FIG. 1.
Figure 2B:
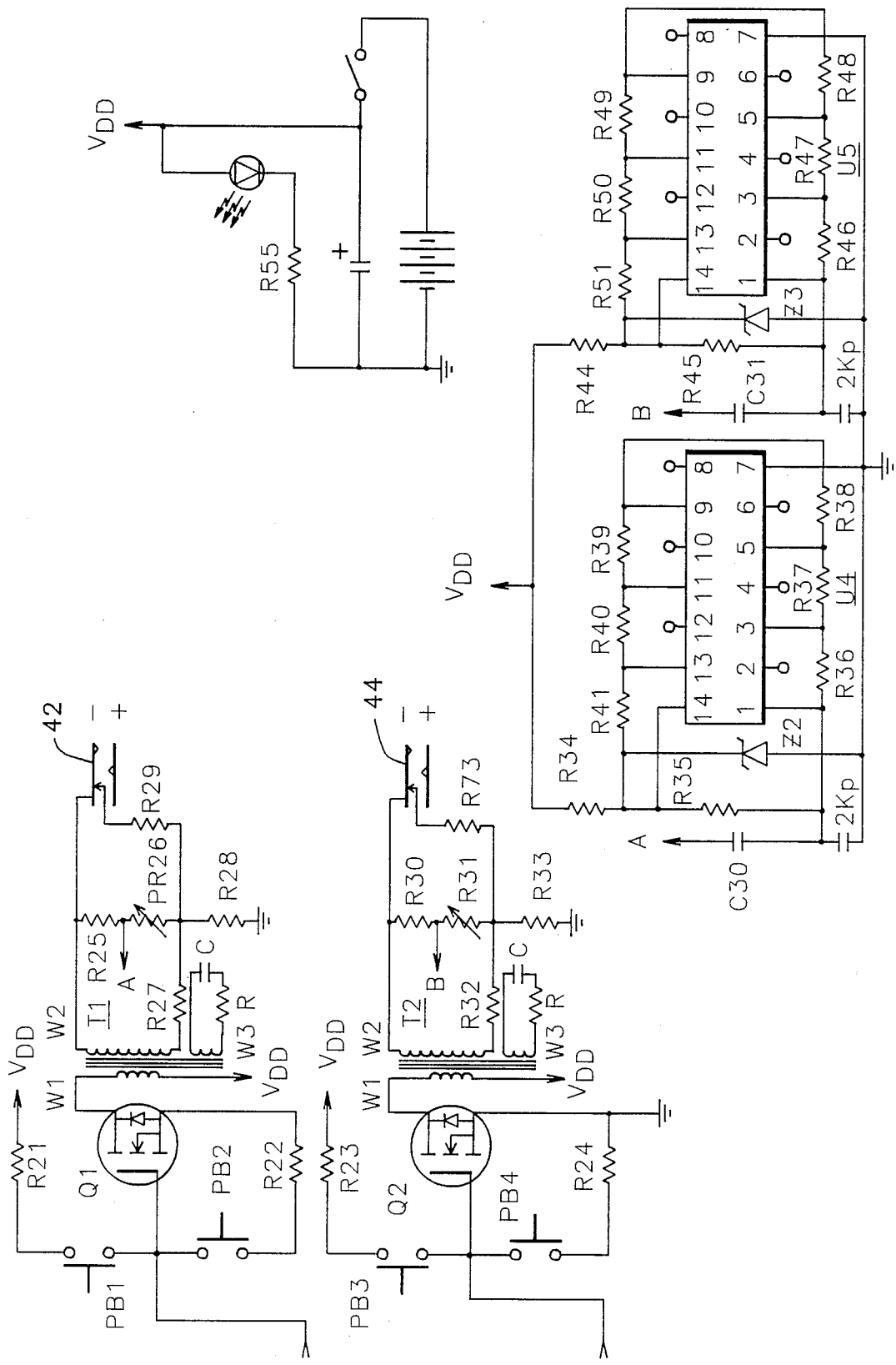

Referring now to FIG. 2, an electronic circuit schematic is shown for implementation of the block diagram of FIG. 1 in accordance with skill of the art electronic design techniques. Pulse generator 10 comprises integrated circuit U3, which may be Motorola MC 154584 B type. Adjustments to the master frequency are accomplished by the combination of resistor R1 and one of the set of capacitors C70-74 via six-position switch 12.

Several ranges of master frequency A are obtainable, from a first range of 0.1 pulse/sec up to 0.7 pulse/sec, with an optimal value of 0.5 pulse/sec. The second range is from 0.8 to 8 pulse/sec, with an optimal value of 1 pulse/sec. The third range is from 9 to 24 pulse/sec, with an optimal value of 12.5 pulse/sec. The fourth range is from 25 to 125 pulse/sec, with an optimal value of 25 pulse/sec. The fifth range is from 180 to 500 pulse/sec, with an optimal value of 280 pulse/sec. The sixth range is a continuous frequency consisting of the carrier frequency.

The carrier frequency (B) is provided at pin 12-13 of U3, by the RC combination R60-61-62, and C60. The carrier frequencies for the preferred embodiment included 1000 pulse per second, 2500 pulse/sec, and 4000 pulse sec. In addition, pins 10-11 of U3 provide the optional frequency (D) as a 100 KHz signal for modulating the output of the pulse train when switch S1 is closed. The RC combination comprising resistor R2 and capacitor C2 provides a linearly increasing and linearly decreasing modulation of the combined frequency envelope, by application of the third frequency (C).

Integrated circuit U3 is protected by a low voltage Zener diode Z1 to maintain stabilized generation of the output frequencies. When the voltage falls below the Zener diode voltage, the Q6 transistor is turned on and the LED is lit to indicate this condition, requiring battery B1 replacement (VDD=5 volt).

Integrated circuit U1, which may be a National MM74C221N type, is the dual monostable multivibrator of blocks 16 and 18, which provides a fixed frequency of the individual pulse duration at a value of 100 microseconds, and with a very fast rise and fall time of 1 microsecond. Integrated circuit U2, which may be a Motorola MM74C08N type, provides digital mixer 20 which has two purposes: (1) causing slight randomizing of the output and (2) maintaining equivalent periods of pulse train duration and the intervals between them.

The source follower of blocks 28 and 30 comprise respective transistors Q3 and Q4, which may be BS 170 Motorola N-channel T-FET types, together with resistors R8, R9, R11 and capacitor C11 (R8, R10, R12 and C12 for Q4). The RC combination R9-C11 (R10-C12) is a low pass filter, and the R11-C11 (R12-C12) combination is a high pass filter. The function of the source follower is to provide the first pulse in the pulse train with a higher amplitude than the second pulse, by changing the bias provided the space charge such that the operating point changes. In the same manner, the amplitude of the pulse train envelope increases gradually until the end of the pulse train.

In accordance with the unique design of the present invention, the fine regulation blocks 32 and 34 provide smooth regulation of the current output by electronic circuitry without mechanical moving parts (electronic helipot). The fine regulation blocks 32 and 34 comprise respective transistors Q1 and Q2, which may be MTP 14N05A Motorola T-FET power transistors, high Q memory capacitor C20 (tantalum type), and regulation resistors R21 and R22 (C21, R23 and 24 for channel II).

The inventive electronic helipot arrangement is capable of infinitely smooth ratio of current regulation, and is based on use of C20 as a storage capacitor for holding the voltage appearing at either of resistors R21 or R22, depending on the time duration of depression of one of respective pushbuttons PB1 or PB2 (PB3 or PB4 for channel II).

A simple digital voltmeter arrangement for measuring the potential applied to the electrodes 42 and 44, is provided by blocks 46 and 48, each of which comprises a hex Schmitt trigger provided by integrated circuits U4 and U5, which may be Motorola MC 14584 HB types. Pins 2,4,6,8,10 and 12 of each of U4 and U5 activate a group of six LEDs for providing a visual indication of the applied potential.

Pulse transformers T1 and T2, typically MnZn ferrite types, are provided to maintain the necessary ratio of current and voltage in accordance with the ratio of primary (W1) and secondary (W2) windings, in order to stimulate the biological tissue. It is a particular feature of the present invention that an optimal pulse shape and constant level of pulse current are provided, in order to obtain a desired physiological response. For this purpose, a third coil W3 is provided in each pulse transformer T1 and T2 which introduces a reactive component related to impedance variations in the body, for example, using a hysteresis constant of B=0.5. This arrangement satisfies the matching impedance criterion for enabling optimal pulse energy transfer to the biological tissue.

While not wishing to be bound by theory, it is believed that the beneficial effects of treatment using the inventive device can be atributed to the physiological behavior of the nervous system and the intercellular tissue. In accordance with the principles of the present invention, it has been recognized that the large nerves have a short refractory period and fast response to externally-introduced electrical signals. These nerves have a myelin layer which partially isolates the electrical signal (Schwann cell). To penetrate this isolation and the intercellular tissue, application of the electrical pulses is achieved by three techniques: 1) use of an appropriate frequency which is within the range of response of the large nerve; 2) use of a pulse waveform which reduces the effect of dielectric losses in the tissue; and 3) combination of the frequency and the pulse shape so as to create a compound of sodium chloride which is released from the nerve membrane, thereby increasing the tissue conductance.

Figure 3A:
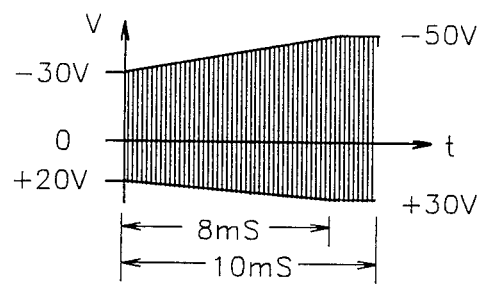
FIGS. 3a–c show respectively, a sample pulse having an increasing amplitude, a randomly appearing pulse, and a linearly modulated pulse and the inverse thereof.
Figure 3B:
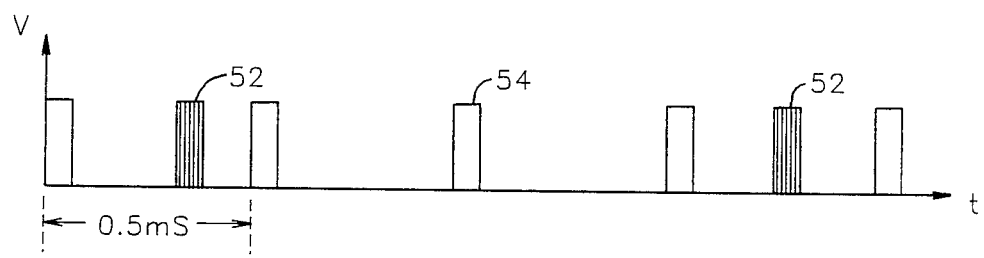
Figure 3C:
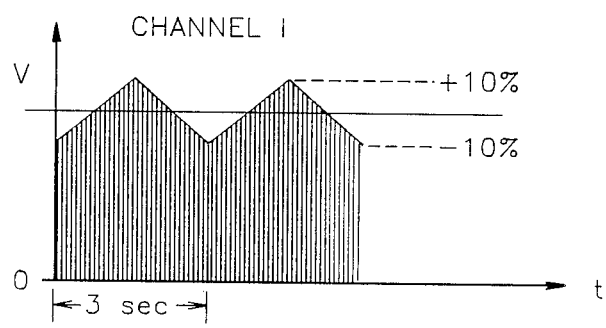
Figure 3C:
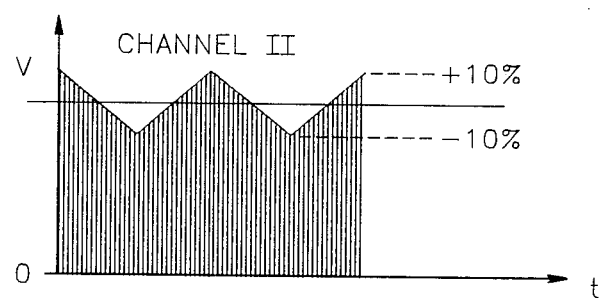

In operation, the inventive neuro-stimulator applies these techniques by developing a pulse train in an appropriate frequency range with a very fast rise and fall time of individual pulses. Referring now to FIGS. 3a-c, there are shown sample pulse waveforms which suit the criteria of the inventive technique as outlined above. In FIG. 3a, a pulse train is shown in which a gradually increasing amplitude is provided during approximately the first 8 msec, in order to avoid a shock reaction of the patient. FIG. 3b shows a random pulse 52 appearing between carrier frequency pulses 54 by combination of the master and carrier frequency (A and B), which are asynchronously generated and mixed by digital mixer 20. The monopolar square wave pulse shape is actually the output from the AND gate, although after modification by the current amplifiers and pulse transformers T1 and T2, the output appears as in Photograph 6.

In FIG. 3c, a sample modulated pulse waveform is shown which exhibits a linearly increasing and decreasing amplitude on its envelope within a 3 second period (approximately), with a deviation of ±-10% variation of the amplitude. This modulation (provided by frequency C) is for the purpose of avoiding accomodation or adaptation of the nervous system to the treatment. This pulse waveform is applied to one electrode and is applied in an inverse fashion to the second electrode by introduction of a time lag provided by inverter 31. The inverse application of the two channel waveform to the extensor and flexor muscles has a beneficial effect on the circulatory system.

Additionally, the inventive neuro-stimulator device is capable of providing sequential type stimulation of two different areas on the skin to affect different nerves in seuential fashion. Thus, selective stimulation of specific nerves without interference from other nerves can be achieved by this technique.

Figure 4A:
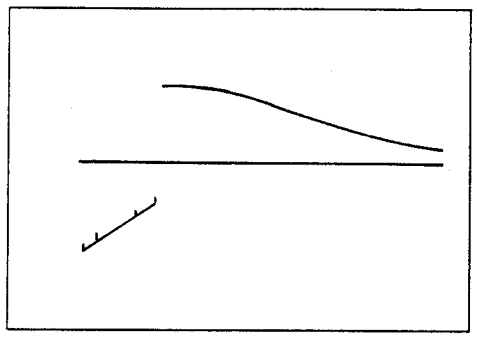
FIGS. 4A–4H show sample pulse waveforms obtained by operation of the inventive neuro-stimulator.
Figure 4B:
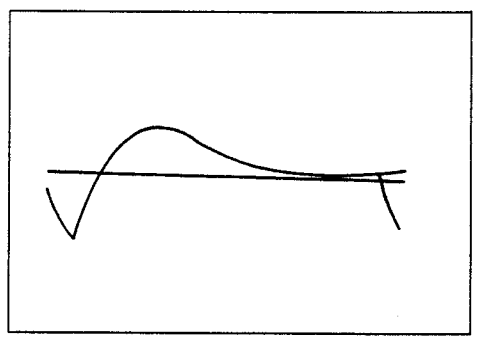

In FIGS. 4A-4H, there are shown pictures of oscilloscope waveforms obtained using the inventive device and a high-speed camera. FIG. 4A represents the negative portion of a sample current pulse having a very fast rise and fall time, and is nearly square-shaped with a pulse width of 100 microseconds. The positive portion of this pulse has an integral which is greater than that of the negative portion, which represents a greater charge capacity, consequently more charge is accumulated by the tissue. The result of this imbalance in the positive and negative integrals causes the sodium ion conductance to be activated, because it is voltage-dependent. The positive portion of the pulse is related to the potassium ion conductance, which is charge-dependent. FIG. 4B shows the corresponding voltage pulse to that of FIG. 1.

Figure 4C:
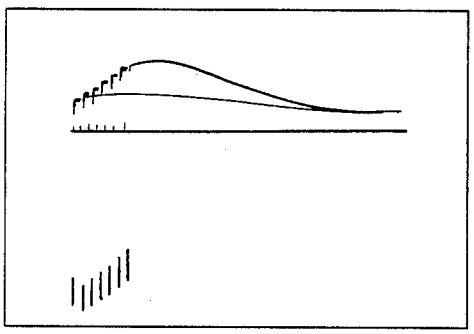
Figure 4D:
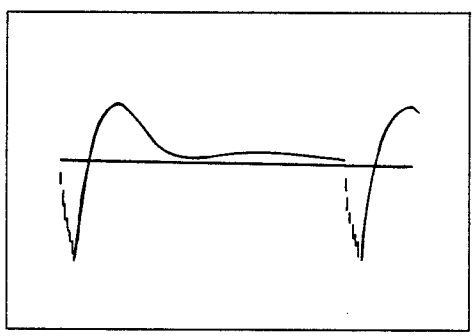

FIG. 4C shows the current pulse of FIG. 1 when modulated by a 100 KHz frequency (optional frequency D) provided by pulse generator 10. The 100 KHz optional frequency increases the penetration of the pulse waveform with reduced dielectrical losses. FIG. 4D represents the voltage form of the pulse corresponding to Photograph 3. The step function potential of the negative portion of the pulse (indicated by the broken trace) is created by the internal capacitance of the tissue.

Figure 4E:
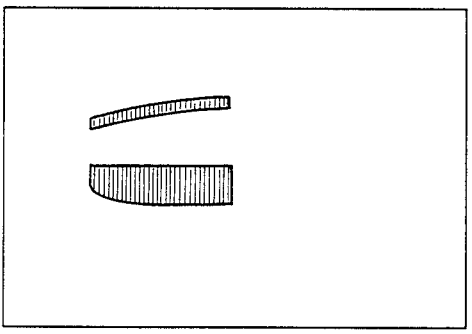
Figure 4F:
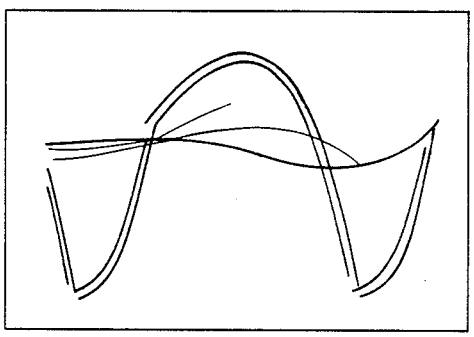

FIG. 4E illustrates the approximate 8 msec period during which the pulse amplitude increases, as described earlier in connection with FIG. 3a. FIG. 4F shows the random pulse (appearing as the lightly contrasted trace existing in different phases) formed as a combination of the master and carrier frequency (A and B).

Figure 4G:
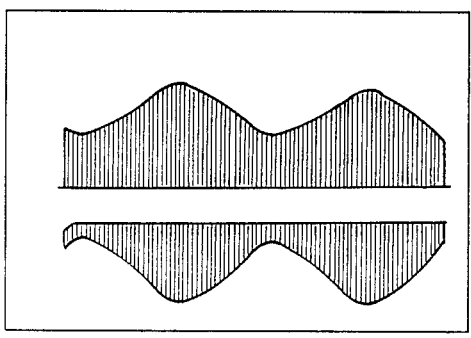
Figure 4H:
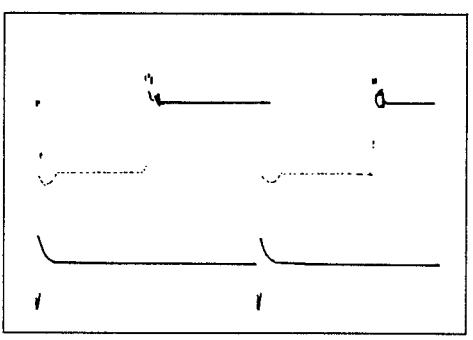

In FIG. 4G, there is shown an approximately 3 second modulation provided by frequency C, together with the inverse waveform, respectively appearing on channels I and II, with a time lag of 1.5 seconds between them. In FIG. 4H, there are shown high energy and low energy pulses corresponding to channels I and II, with the high energy pulse being applied for pain relief and the low energy pulse being applied only for motor nerve activation. This latter waveform is useful for diagnostic purposes to estimate the threshold potential of the motornerves, applying the technique of myography. Alternatively, using the visual indication of the applied potential provided by the LEDs of blocks 46 and 48, the threshold potential of the motornerve may be estimated when the muscle twitch is observed.

Based on its unique design and the operating programs provided for determining particular pulse characteristics and combinations thereof, the inventive neuro-stimulator has been shown to achieve excellent clinical performance in therapeutic treatment of pain and stimulation of muscles.

Having described the invention in connection with certain specific embodiments thereof, it is to be understood that the description is not meant as a limitation since further modifications may now suggest themselves to those skilled in the art and it is intended to cover such modifications as fall within the scope of the appended claims.

I claim:

1. An electrical neuro-stimulation apparatus comprising:

first pulse generation means for providing a first variable frequency and pulse width output;

second pulse generation means for providing a second variable frequency and pulse width output;

switching means for providing a series of successive pulse trains as a combination of said first and second pulse width outputs on at least one output channel, wherein for each of said series of successive pulse trains, the period of said pulse train duration and the interval between it and the next successive pulse train are substantially equivalent, and random pulses appear in said series of successive pulse trains in accordance with digital mixing of the output of said first and second pulse generation means;

means for modulating said series of successive pulse trains so as to provide a pulse waveform envelope having an increasing amplitude during a predetermined interval; and current amplification means for providing said modulated series of successive pulse trains to at least one pair of electrodes with substantially constant current in relation to behavioral changes in tissue impedance for increased penetration, said amplified modulated series of pulse trains adapted to provide electrical stimulation of the large myelinated nerves, said stimulation having associated therewith the characteristics of significantly increased energy and relatively low skin irritation and pain levels.

2. The apparatus of claim 1 wherein said modulating means comprises a source follower FET configuration providing said waveform envelope shape by application of a space-charge-activated FET effect in accordance with high and low pass filter operation.

3. The apparatus of claim 1 wherein said current amplification means comprises a pulse transformer providing a reactive component in accordance with said behavioral changes of said tissue impedance for maintaining an optimal pulse waveform shape and substantially constant current.

4. The apparatus of claim 1 further comprising first and second modulation frequencies, said first modulation frequency providing a triangular form of amplitude modulation on a first output channel and an inverter means providing a 180 degree shift in said first modulation frequency on a second output channel to avoid a physiological accomodation phenomena.

5. The apparatus of claim 4 wherein said second modulation frequency provides 100 KHz modulation to reduce dielectrical loss in the tissue.

6. The apparatus of claim 1 wherein said current amplification means provides current regulation with an infinitely smooth ratio based on external pushbutton-controlled application of voltage to a storage capacitor which holds a bias voltage on T-FET power transistor.

7. The apparatus of claim 1 further comprising a set of LEDs for providing a visual indication of the applied potential produced by said amplified modulated series of pulse trains, said LEDs being driven by a Hex Schmitt trigger and representing the peak voltage of a single pulse.

8. The apparatus of claim 7 wherein said visual indication is calibrated by association with said LEDs, each representing a value of said peak voltage, for use as a threshold response measurement in observation of mechanical muscle response to said electrical stimulation.

9. The apparatus of claim 1 wherein a visual indication of a low power supply condition is provided by an LED in series with a switching transistor, wherein said LED is lit when said power supply is below a predetermined voltage level.

10. A method of providing electrical stimulation comprising the steps of:
generating a first variable frequency and pulse width output;
generating a second variable frequency and pulse width output;
combining said first and second pulse width outputs on at least one output channel to produce a series of successive pulse trains, wherein for each of said series of successive pulse trains, the period of said pulse train duration and the interval between it and the next successive pulse train are substantially equivalent, and random pulses appear in said series of successive pulse trains in accordance with digital mixing of the output of said first and second frequency generating steps;
modulating said series of pulse trains so as to provide a pulse waveform envelope having an increasing amplitude during a predetermined interval; and
amplifying said modulated series of pulse trains such that there is provided to at least one pair of electrodes an output with substantially constant current in relation to behavioral changes in tissue impedance for increased penetration, said amplified modulated series of pulse trains providing electrical stimulation of the large myelinated nerves, said stimulation having associated therewith the characteristics of significantly increased energy and relatively low skin irritation and pain levels.

11. The method of claim 10 wherein said modulating step comprises triangular amplitude modulation at a slow rate of approximately 3 seconds.

12. The method of claim 11 wherein said triangular amplitude modulation is provided with a phase shift of 180 degrees by use of a time lag between a pair of output channels.

13. The method of claim 10 wherein said amplifying step comprises relatively slow current regulation by memory storage of a predetermined externally-adjustable voltage for regulation of output current to the electrodes.

14. The method of claim 10 further comprising the step of providing a visual indication of the applied potential produced by said amplified modulated series of pulse trains, said visual indication being calibrated for use as a threshold response measurement in observation of mechanical muscle response to said electrical stimulation.

15. The method of claim 12 wherein said amplifying step provides compensation for changes in the tissue impedance by self-adjustment of the amplitude of said modulated pulse trains.

* * * * *